United States Patent
Berghmans et al.

(10) Patent No.: US 7,071,469 B2
(45) Date of Patent: Jul. 4, 2006

(54) PROCESS FOR IDENTIFYING OBJECTS USING AN OPTICAL SPECTROMETER AND A TRANSPORT SYSTEM

(75) Inventors: Antonius Christianus Berghmans, Maastricht (NL); Michel Joseph Germain Huys, Hasselt (BE)

(73) Assignee: DSM IP Assets B.V., Heerlen (NL)

( * ) Notice: Subject to any disclaimer, the term of this patent is extended or adjusted under 35 U.S.C. 154(b) by 51 days.

(21) Appl. No.: 10/275,656

(22) PCT Filed: May 9, 2001

(86) PCT No.: PCT/NL01/00355

§ 371 (c)(1),
(2), (4) Date: Nov. 8, 2002

(87) PCT Pub. No.: WO01/86267

PCT Pub. Date: Nov. 15, 2001

(65) Prior Publication Data

US 2003/0111606 A1 Jun. 19, 2003

(30) Foreign Application Priority Data

May 10, 2000 (EP) ................... 00201671
May 10, 2000 (EP) ................... 00201672
May 10, 2000 (EP) ................... 00201673

(51) Int. Cl.
*G01N 21/35* (2006.01)
(52) U.S. Cl. .................. 250/339.01; 209/577
(58) Field of Classification Search .......... 250/339.01; 209/577
See application file for complete search history.

(56) References Cited

U.S. PATENT DOCUMENTS

| 5,401,954 | A | | 3/1995 | Richert |
| 5,850,623 | A | * | 12/1998 | Carman et al. ............... 702/28 |
| 5,952,660 | A | | 9/1999 | Kip et al. |
| 6,262,419 | B1 | | 7/2001 | Huth-Fehre et al. |
| 6,313,423 | B1 | * | 11/2001 | Sommer et al. ............ 209/587 |

FOREIGN PATENT DOCUMENTS

| FR | 1292819 | 10/1962 |
| GB | 916641 | 1/1963 |
| WO | 97/25605 | 7/1997 |
| WO | WO 9819800 A1 * | 5/1998 |
| WO | 98/46372 | 10/1998 |
| WO | 99/06160 | 2/1999 |
| WO | 99/27623 | 6/1999 |

* cited by examiner

Primary Examiner—David Porta
Assistant Examiner—Shun Lee
(74) Attorney, Agent, or Firm—Mayer, Brown, Rowe & Maw LLP

(57) ABSTRACT

A process and an apparatus are useful for identifying articles which are at least partly made from at least one polymer. The process and apparatus use an optical spectrometer and a transport system, whereby the articles to be identified are moved by the transport system past the optical spectrometer, where they are irradiated, response measured and analyzed. An external reference object is also transported, by the transport system, past the optical spectrometer such that it becomes possible to use the measured response for the reference object to identify, with greater accuracy, the articles to be identified.

22 Claims, 3 Drawing Sheets

PROCESS FOR IDENTIFYING OBJECTS USING AN OPTICAL SPECTROMETER AND A TRANSPORT SYSTEM

CROSS REFERENCE TO RELATED APPLICATION

This application is the National Phase of International Application PCT/NL01/00355 filed May 9, 2001 which designated the U.S., the entirety of which is incorporated herein by reference.

The invention relates to a process for identifying articles which are at least partly made from at least one polymer, using an optical spectrometer and a transport system, said process comprising the steps of:
a) moving the articles past the optical spectrometer using the transport system
b) irradiating the articles and measuring the response of the irradiated articles using the optical spectrometer, analyzing the response to identify the articles as to the type of polymer.

Such a process is known from WO-A-9725605.

In the process described in WO-A-9725605 the articles are identified using infrared spectroscopy, while the articles are moved past the infrared spectrometer, for instance using a continuously driven belt. The articles are irradiated, and recognized based on the information included in the spectrum which the articles reflect. The articles may then be transported to a location in accordance with the identification.

In particular if the spectra of the different types of polymers are only slightly different, which is for instance the case for different types of polyamides, such as for instance polyamide-6 and polyamide-6,6, small variations in the measuring conditions can make the distinction between such polymers difficult. In particular if a transport system is used to move the articles past the optical spectrometer, it is difficult to prevent variations in the measuring conditions. A cause of such variations is for instance a fluctuation in temperature, a fluctuation in humidity and the generation of dust during transport, in particular in a large-scale process. A lot of dust may in particular be generated if the articles are waste articles or used articles. Other variations in measuring conditions include for instance variations in the intensity of the light source and variations in the detector.

It is an object of the invention to provide a process in which articles having a polymer surface, can be effectively identified as to the type of polymer, using a transport system.

This object is achieved according to the invention by providing a process for identifying articles which are at least partly made from at least one polymer, using an optical spectrometer and a transport system, said process comprising the steps of:
a) moving the articles past the optical spectrometer using the transport system
b) irradiating the articles and measuring the response of the irradiated articles using the optical spectrometer, analyzing the response to identify the articles as to the type of polymer characterized in that the process also comprises the step of
c) at least periodically irradiating an external reference object, measuring the response of the irradiated reference object using the optical spectrometer, and using the measured response for the analysis of step b).

According to the invention an effective identification is achieved, even if the polymers exhibit only a slightly different response, such as for instance polyamid-6 and polyamid-6,6. According to the invention, the articles can be transported at high speed past the optical spectrometer, while keeping the fraction of correctly identified articles high.

It is noted that U.S. Pat. No. 5,952,660 describes a hand-held infrared spectrometer for discriminating between polyamide-6 and polyamide-6,6. In this publication it is described that a reference measurement is performed. For the hand-held infrared spectrometer built in accordance with U.S. Pat. No. 5,952,660, an internal reference object is used, i.e. a reference object which is inside the housing of the spectrometer.

As an external reference object may be used any reference object which is placed outside the optical spectrometer. An optical spectrometer generally comprises a light source for irradiating the articles to be identified, a detector for measuring the response of the irradiated articles and a wave length selector. The spectrometer may also comprise a housing in which the light source and the detector, and optionally, the wave length selector are present. If the spectrometer comprises a housing in which the light source and the detector are present, any reference object which is placed outside the housing may be used as an external reference object. If the spectrometer does not comprise a housing in which the light source and the detector are present, any reference object may be used as an external reference object.

Preferably a reference object is used having a surface of a known material and/or of a material having surface properties which do not substantially change over time. Examples of suitable reference materials having surface properties which do not substantially change over time include ceramic materials, metals which do not substantially oxidize in the atmosphere, such as for instance, copper, brass, metals having a protective oxide layer, such as for instance stainless steel or aluminum. Polymer reference materials having surface properties which do not substantially change over time may also be used, such as for instance Teflon or polystyrene. Preferably, the surface properties of the reference object are such that diffuse reflection is achieved upon irradiation. This improves the accuracy of the measurement. Such surface properties may for instance be achieved by roughening the surface, for instance by grinding and/or sand blasting.

The measured response of the irradiated reference object is used for the analysis of step b), i.e. for the analysis of the response of the irradiated articles to identify the articles as to the type of polymer. In a preferred embodiment, the response of the irradiated reference object is used for correction of background signals. In this embodiment the measured response of the reference object may be used for the calculation of the absorption according to formula 1.

$$A_\lambda = -\log(I_{\lambda(article)}/I_{\lambda(reference\ material)}) \quad (1)$$

where $A_\lambda$ is the absorption at wavelength $\lambda$ and $I_\lambda$ is the light intensity of the reflected light at wavelength $\lambda$. The calculated absorption may then be further analyzed to identify the articles as to the type of polymer. For said analysis the data are preferably subjected to a pre-treatment, such as for instance smoothing, taking a derivative or normalization. Said pre-treated data may subsequently be subjected to classification and/or qualification. Methods known in the art, such as for instance a principle component analysis, partial least square analysis, or multi-linear regression may advantageously be used. Suitable techniques are described in "Multivariate Calibration", by Harald Martens and Tormod Naes, John Wiley & Sons (1991) Great Brittain. The calculated values for the absorption are preferably processed, and the processed data may be compared with known data for known types of polymer. For instance, in a principle component analysis, known data for known polymers may be used to define a box in a two-dimensional plot. The processed data of the articles to be identified may be plotted in the same two-dimensional plot. If the processed data of the articles fall within a box corresponding to a known type of polymer, the article to be identified is recognized as the type of polymer corresponding to said box.

In another preferred embodiment, the response of the irradiated reference object is used for correction for drift. This embodiment further improves the accuracy of the identification. In this embodiment, the reference object has preferably a surface made from a known polymer, said known polymer being one of the polymers to be identified. By at least periodically irradiating and measuring the response of said surface, the drift, i.e. the change of the response over time for a polymer, may be determined. Said change may then be used to change the known data for said polymer, for instance by shifting the position of the above-mentioned box in the two-dimensional plot.

It is to be understood that more than one reference object may be at least periodically irradiated. It is for instance possible, that the response of a reference object, preferably having surface properties which do not substantially change over time, is used for correction of background signals, and that one or more other reference objects, preferably having a surface of one or more of the polymers to be identified, is used for the correction of drift. It is possible that more than one reference objects are combined to form one structure having surfaces of different reference materials.

At least periodically an external reference object is irradiated, and the response of the irradiated reference object is measured using the optical spectrometer. With "At least periodically" is meant at intervals or continuously. Usually the irradiation of the external reference object, and the measuring of the response of the irradiated object is performed at intervals. It is possible that the intervals are equal to each other, but this is not necessary. The preferred intervals between the reference measurements may depend on the extent to which variations in the measurement conditions occur and on the extent to which the responses of the irradiated articles are similar. If the variations in the measurement conditions vary to a high extent, it is desirable that the intervals between the reference measurements is relatively short. If the spectra of the polymers to be distinguished are only slightly different, it also desirable that the intervals between the reference measurements are relatively short. The reference object may advantageously be moved past the optical spectrometer using endless transport means, such as for instance an endless transport rail or an endless belt. The reference measurement may then be performed every time that the reference object is moved past the optical spectrometer. Most preferably the reference object is moved past the optical spectrometer using the transport system. This allows the reference measurement, i.e the irradiation of the reference object and the measurement of the response, to be carried out in an effective way without interrupting the transport of the articles.

Preferably, the reference object is moved past the optical spectrometer while it is irradiated. This is in particular advantageous when the articles to be identified are also moved past the optical spectrometer while they are irradiated. This allows the reference object to be irradiated in a way comparable to that of articles to be identified, which improves the accuracy.

In a preferred embodiment, the reference object is fixed to the transport system and the fixed reference object is moved past the optical spectrometer and irradiated. This allows the reference object to be moved past the spectrometer in a predetermined position, which improves the accuracy of the measurement. A predetermined position of the reference object may for instance be a predetermined distance to the spectrometer during irradiation and/or a predetermined angle with the irradiation beam during irradiation. Fixing the reference object to the transport system may for instance be carried out by fixing the reference object to a movable belt of a conveyor or to means, for instance a carriage, which are movable along a transport rail.

In a particularly preferred embodiment the reference object and the articles are fixed to the transport system, and the fixed reference object and fixed articles are moved past the optical spectrometer, and irradiated. Fixing the reference object and the articles to the transport system allows the reference object and the articles to be moved past the spectrometer in a predetermined position, which improves the accuracy of the identification. A predetermined position of the articles may be for instance a predetermined distance to the spectrometer during irradiation and/or a predetermined angle with the irradiation beam during irradiation. It will be understood that the predetermined position of the articles and the predetermined position of the reference materials are not necessarily the same. However, it is advantageous if the predetermined distance from the reference object to the spectrometer during irradiation and the predetermined distance from the articles to the spectrometer during irradiation is approximately the same. Fixing the articles to the transport system may for instance be carried out by fixing the articles to a movable belt of a conveyor or to means, for instance a carriage, which is movable along a transport rail. Preferably, the transport system comprises a transport rail and the reference object and articles are fixed to the transport rail, and the fixed reference object and fixed articles are moved past the optical spectrometer, and irradiated. This embodiment allows a very accurate identification of the articles. This embodiment is in particularly advantageous if the articles are textile materials, such as for instance carpets and/or carpet materials.

In a preferred embodiment, separate detecting means are used for detecting when a reference object is in front of the optical spectrometer. This is a simple and effective way for recognizing that a reference object is in front of the spectrometer. Separate detecting means are understood to be any suitable means for detecting the presence of a reference object, apart from the spectrometer itself. A light sensor or a mechanical sensor may advantageously be used.

In a preferred embodiment, a predetermined surface the articles and/or reference object is irradiated and the process also comprises the step d) of determining when the predetermined surface of the articles and/or reference objects is in front of the spectrometer, and starting the irradiation, measuring and/or analyzing the response, for each article and/or reference object individually, while the predetermined surface of said individual article and/or reference object is in front of the spectrometer. The predetermined surface is preferably a surface which is in a predetermined position, for instance having a predetermined angle with the irradiation beam or having a predetermined distance to the spectrometer, when irradiated by the irradiation beam. Preferably, the irradiation, measuring the response, and/or analyzing the response is stopped while the predetermined surface of said individual article and/or reference object is in front of the spectrometer. This embodiment is in particular advantageous when a predetermined surface of flexible articles, for instance textile article, in particular carpets, is irradiated. Such predetermined surface may be a part of an article which can be irradiated through an opening in a clamp, said clamp fixing the article to the transport system. As used herein "in front of the spectrometer" denotes that the predetermined surface can be reached by the irradiation beam or irradiation beams of the optical spectrometer. As used hereing "starting the analyzing of the response while the predetermined surface is in front of the optical spectrometer" denotes analyzing a set of data which have been measured during a time interval, the start of said time interval being within a period within which the predetermined surface is in front of the optical spectrometer. It is possible that separate detecting means are used for detecting when a the predetermined surface is in front of the optical spectrometer. This is a simple and effective way for recognizing that the predetermined surface is in front of the spectrometer. Separate detecting means are understood to be any suitable means for detecting the presence of an article, apart from the optical spectrometer. A light sensor or a mechanical sensor may advantageously be used.

The invention is not limited to a specific type of optical spectrometer. A Raman spectrometer may for instance be used. Preferably, the optical spectrometer is an infrared spectrometer. As used herein infrared spectrometers also include mid-infrared spectrometers and near-infrared spectrometers. A very suitable spectrometer has been described in WO-A-9725605, the contents of which are herewith incorporated by reference. A near-infrared spectrometer is very suitable for distinguishing between polyamide-6 and polyamide 6,6.

The process according to the invention is in particular suitable, if at least part of the articles are at least partly made from a polyamide, for instance polyamide-6 and/or polyamide 6,6. The process according to the invention is very well suitable to distinguish between polymers of which the spectral response following irradiation is only slightly different, such as for instance polyamide-6 and polyamide-6,6. If it is to be distinguished between polyamide-6 and polyamide-6,6, PET and polypropylene, which are typical materials for face fibres of carpets, it is advantageous to use spectral information in the range of 1000 to 3000 nm, preferably 2000 to 2600 nm.

The process according to the invention is very suitable if the articles are textile articles, more in particular carpet or carpet materials, most in particular waste textile articles, carpets or carpet materials.

The transport system is not limited to a specific kind of transport system. A conveyer may for instance be used. Preferably, a transport system is used which comprises a transport rail, to which the articles can be movably connected. A suitable transport system of this type has been described in WO-A-9906160, the contents of which are herewith incorporated by reference.

The invention also relates to an apparatus for identifying articles, in particular textile materials and/or carpets, said apparatus comprising:
 a) an optical spectrometer (1)
 b) a transport system, said transport system comprising a transport rail (2) and transport units (3), the transport units comprising a body (4), clamping means (5) for fixing the articles (6) to the transport units, the transport units being movably connected to the transport rail c) a guide system (8,9) which is capable of cooperating with the body and/or clamping means, said guide system at least being present in the area of the optical spectrometer.

When this apparatus is used, the accuracy of the identification is improved.

In a preferred embodiment the guide system comprises a guiding element which is essentially parallel to the transport rail, said guiding element being capable of cooperating with the body and/or coupling means. The guiding element may for instance be a guide rail. Preferably, the body and/or coupling means comprise one or more guiding members which can cooperate with the guiding element. More preferably, the body and/or coupling means comprise at least two guiding members which can cooperate with the guiding element. Preferably, the guiding members are rotatable elements, such as for instance wheels.

In a preferred embodiment the guide system comprises a pair of guiding elements which are essentially parallel to the transport rail and which are capable of receiving the body and/or coupling means. The pair of guiding elements may for instance be a pair of guide rails.

In a preferred embodiment, the guide system is a transversal guide system. A transversal guide system includes any system which is capable of preventing movement of the body and/or coupling means in the transversal direction, in particular in the direction of the irradiation beam or irradiation beams of the optical spectrometer.

In another preferred embodiment, the guide system is a longitudinal guide system. A longitudinal guide system includes any system which is capable of preventing movement of the body and/or coupling means around the transversal direction, in particular around an axis parallel to the irradiation beam or the irradiation beams of the optical spectrometer.

Most preferably, the guide system includes a transversal guide system and a longitudinal guide system.

Preferably, the coupling means have openings through which an article which is coupled with said coupling means can be irradiated with an irradiation beam.

In a preferred embodiment the coupling means are up and downward movable, the body is provided with a pulley for the up and downward movement of the coupling means, the pulley is movable by a friction element and a contact rail is present in the area of the optical spectrometer which can cooperate with the friction element.

As a carriage may be used any means which can be movably fixed to the transport rail. The body forms the connection between the carriage and the coupling means.

DETAILED DESCRIPTION OF A PREFERRED EMBODIMENT

Figure 1:
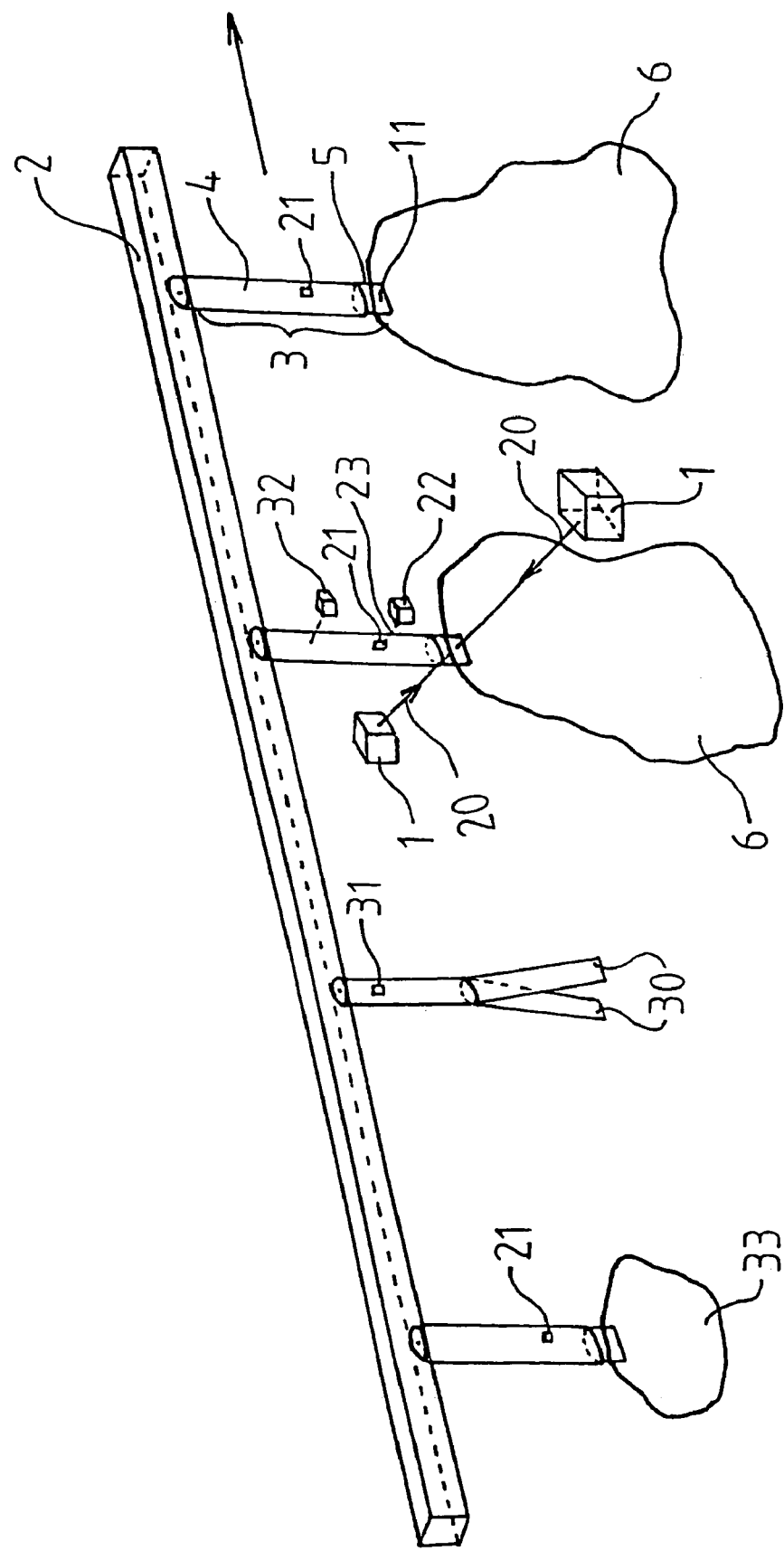
FIG. 1 shows a schematic view of a preferred embodiment of the process according to the invention.

A preferred embodiment of the invention is described with reference to FIG. 1. Articles to be identified, in this case carpets (6) or pieces of carpet, fixed to transport rail (2) via transport units (3) and clamps (5), are moved past two near-infrared (NIR) spectrometers (1) in the direction as indicated by the arrow, for instance at a rate of 1000 m/s.

Transport rail (2) is an endless rail which forms a loop (not shown). Fixing the carpets (6) to transport rail (2) takes place before they are moved past NIR-spectrometers (1). During movement of the carpets (6) past NIR-spectrometers (1) a part of the surface area of carpets (6) is irradiated by irradiation beams (20) of NIR-spectrometers (1). Carpets (6) are irradiated via an opening (11) in clamps (5). The irradiated parts of the carpets are in a transverse position during irradiation. Diffuse reflectance is measured using a detector (not shown) in NIR-spectrometers (1). For instance a spectrum covering the range from 2400 to 2510 nm may be measured if it is to be distinguished between polyamide-6, polyamide-6,6, PET, and polypropylene. The measured reflection is analyzed, for which analysis the absorption is calculated using the results of a prior performed reference measurement. The results are further analyzed, for instance by using a principle component analysis, to identify the carpets as to the type of polymer, in this case the type of polymer of the face fibre of the carpets. For this analysis a correction is made for drift using the results of a prior performed reference measurement. Following irradiation the carpet is moved further and released at a location in accordance with its identification. Following the release of the carpets other pieces of carpet to be identified is fixed to the clamps (5).

Reference object (30) is also fixed to transport rail (2), and moved past NIR-spectrometers (1). In this case reference object (30) is a roughened stainless steel plate. The angle of the stainless steel plate with irradiation beam (20) may be adjustable, but this angle is generally kept constant during the course of the process. A second reference object (33), in this case a piece of carpet made from a known polymer, e.g. polyamide-6, and a third reference object, in this case a piece of carpet made from a known polymer, e.g. polyamide-6,6 (not shown), are also fixed to transport rail (2), and moved past NIR-spectrometers (1). If the reference object (30) has come in front of irradiation beams (20), its presence is detected using sensor (32) which detects radiation which is reflected by reflecting patch (31) upon irradiation by the sensor. Following detection of the reference object by the sensor, reference object (30) is irradiated using irradiation beams (20) while being moved past NIR-spectrometers (1). The diffuse reflectance of reference object (30) is detected in the same wave length range as that of the carpets. The measured reflectance from the reference object (30) is used for the calculation of the absorption of the carpets which are subsequently irradiated, until the reference object is irradiated again. During movement of the second (33) and third reference objects past NIR-spectrometers (1) a part of the surface area of reference objects is irradiated by irradiation beams (20) of NIR-spectrometers (1) in the same way as for the carpets to be identified. The measured response from second reference object (33) and third reference object (not shown) is used for the correction of drift. All reference objects remain fixed to the transport rail throughout the process, so that a reference measurement may be performed any time that a reference object is moved past NIR-spectrometers (1). Transport rail (2) may for instance be provided with 50 transport units (3) and with three reference objects (30, 33 and a third one), in which case three reference measurements are performed per 50 carpets.

Description of a Preferred Embodiment for Irradiating an Article

Below, a preferred embodiment is described for irradiating an article with reference to FIGS. 1 and 2. Articles, in this case carpets (6) are fixed to transport rail (2) via transport units (3) comprising a body (4) and clamps (5), the transport units being movable along transport rail (2). Clamps (5) are provided with openings (11) through which a part of the surface of the carpets (the predetermined surface, 6a) can be irradiated with irradiation beams (20) of near-infrared (NIR) spectrometers (1). Transport units (3) are constructed in such a way that rotation around a vertical axis is prevented during movement past NIR-spectrometers (1). During movement past NIR-spectrometers (1) the predetermined part (6a) of carpets (6) in openings (11) are in a predetermined transverse position. Each transport unit (3) is provided with reflecting patch (21) which is detectable by sensor 22 (which is capable of detecting the reflection of sensor irradiation beam (23) which is continuously emitted) at a moment at which the predetermined surface is in front of the irradiation beams (20), which are continuously emitting during the process. At the moment that reflecting patch (21) is detected by sensor (22) measuring of the response of the irradiated predetermined surface is started. The measuring of the response is terminated before the predetermined surface has ceased to be in front of the NIR-spectrometers (1). It will be appreciated that it is also possible that reflecting patch (21) has such a position that it is detectable by sensor (22) at a moment before the predetermined surface is in front of the irradiation beams (20) and that the moment at which the predetermined surface becomes in front of the irradiation beams (20) is derived from the rate at which transport takes place. It will be appreciated that it is also possible that irradiation, measuring the response and analyzing the response are started at the moment that reflecting patch (21) is detected.

Figure 2:
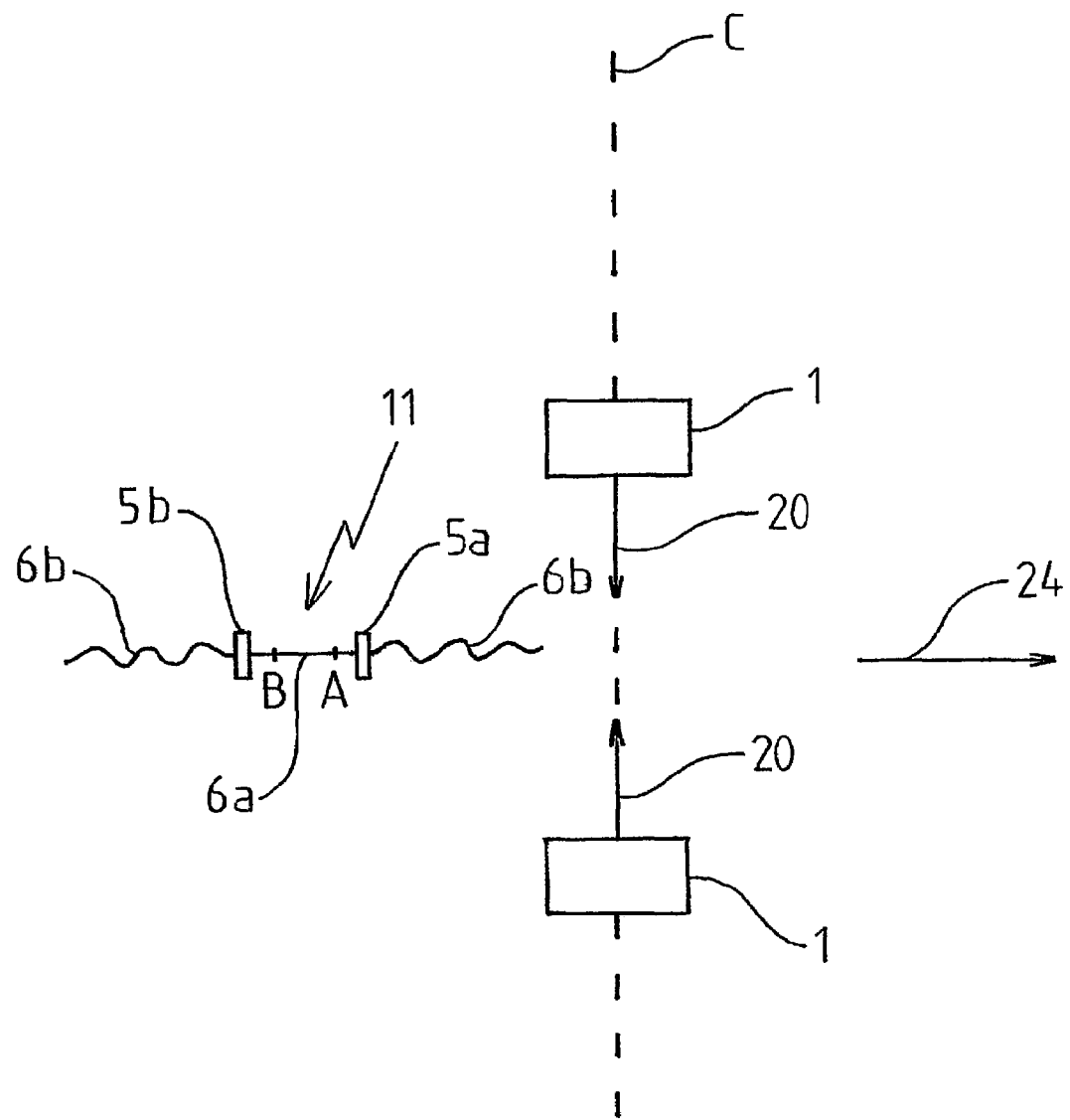
FIG. 2 shows a schematic top view of a preferred embodiment for irradiating an article.

FIG. 2 shows a top view of a the present embodiment. Carpet (6) is fixed in clamp (5) having an opening (11). The distance between both sides (5a and 5b) of clamp (5) is about 3.5 cm. Predetermined surface (6a) of carpet (6) within clamp (5) is in a predetermined position in contrast to the part of the carpet (6b) which is not within the clamp. Carpet (6) is moved in the direction of the arrow (24) at a speed of 1000 m/hour past two NIR-spectrometers (1) having irradiation beams (20) which are continuously emitted. Reflecting patch (21, not shown) is positioned in such a way that the moment is detected at which point A (about 1 cm from clamp side 5a) crosses line C. At that moment measuring of the response is started. Thus, measuring the response is started while predetermine surface (6a) is in front of the optical spectrometers (1). Spectra are measured (range 2400 to 2510 nm) using a detector in the NIR spectrometers (1) (not shown), the measurement time being about 50 ms. At the moment at which the measuring of the response is terminated, point B (about 1 cm from clamp side 5b) crosses line C, so that the measuring is terminated while the predetermined surface is in front of the spectrometers (8).

Description of a Preferred Embodiment in which a Guide System is Present

Figure 3:
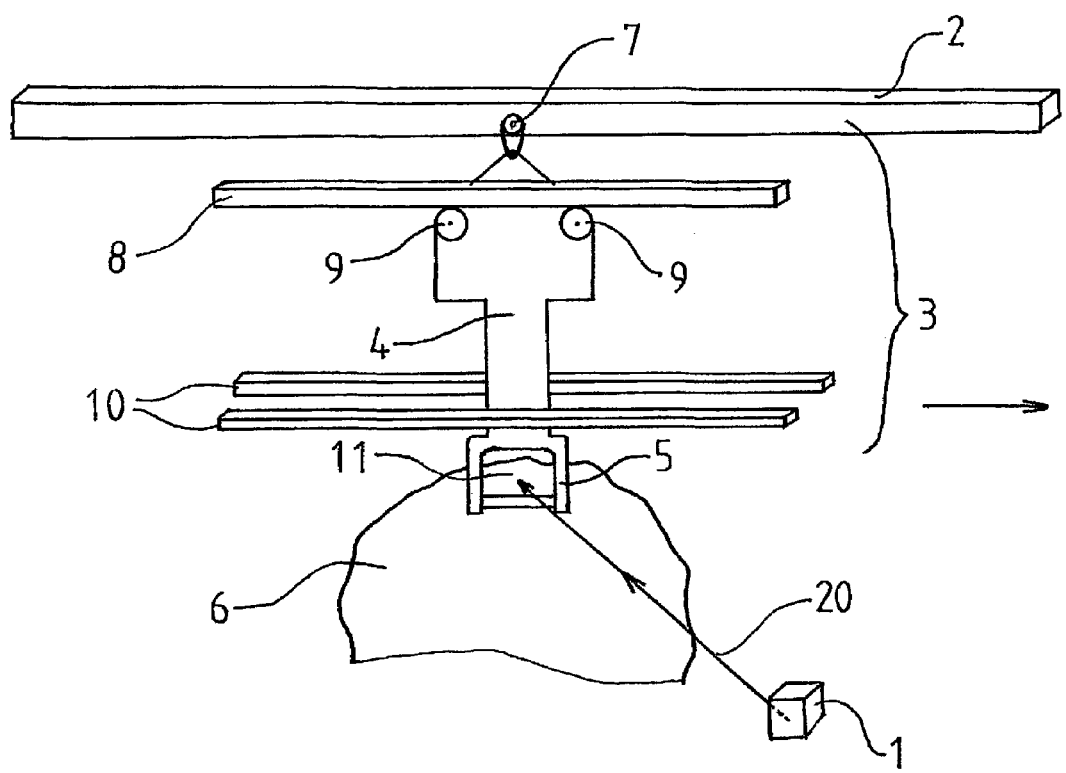
FIG. 3 shows a schematic view of a preferred embodiment in which a guide system is present.

FIG. 3 shows transport rail (2) and one transport unit (3) in the area of near-infrared (NIR) spectrometer (1). The arrow indicates the direction of transport. Transport unit (3) comprises a carriage (7) which can be moved in transport rail (2) using a chain (not shown), clamp (5) (coupling means), and a body (4) which connects clamp (5) and carriage (7). A carpet (6) is fixed to clamp (5), having opening (11) through which a part of carpet (6) can be irradiated with the irradiation beam of optical spectrometer (1). In this figure carpet (6) is in a position that it can be irradiated through opening (11) with irradiation beam (20).

At its upper part, body (4) is provided with two wheels (9) (guiding members) which can cooperate with guide rail (8). The combination of two wheels (9) and guide rail (8) prevent rotation around an axis parallel to irradiation beam (20). This improves the accuracy of the identification. A pair of guide rails (10) (guiding elements) is also present. Body (4) can be guided between said pair of guide rails (10). This prevents movement of the body (4) and clamp (5) in the transverse direction, which improves the accuracy of the identification. An accurate identification can take place during movement of the carpet past NIR spectrometer (1). The transport system may for instance be provided with 50 transport units. The transport rate may for instance be 1000 m/hour.

What is claimed is:

1. Process for identifying articles which are at least partly made from at least one polymer, using an optical spectrometer and a transport system, said transport system comprising a transport rail and transport units, the transport units comprising a body, coupling means for fixing the articles to the transport units, the transport units being movably connected to the transport rail and a guide system which is capable of cooperating with the body and/or coupling means, said guide system at least being present in the area of the optical spectrometer, wherein the guide system comprises a pair of guiding elements which are essentially parallel to the transport rail and which are capable of receiving the body and/or coupling means, said process comprising the steps of:
    a) moving the articles past the optical spectrometer using the transport system;
    b) irradiating the articles and measuring the response of the irradiated articles using the optical spectrometer, analyzing the response to identify the articles as to the type of polymer;
    c) at least periodically irradiating at least one external reference object, using the transport system to move the at least one external reference object past the optical spectrometer, measuring the response of the at least one irradiated reference object using the optical spectrometer, and using the measured response of the at least one external reference object for the analysis of step b) and for correction of background signals and/or for correction for drift.

2. Process according to claim 1, wherein the surface material of a said at least one external reference object is made from one of the polymers to be identified.

3. Process according to claim 2, wherein one of the polymers to be identified is polyamide 6 and/or polyamide 6,6 and that the surface material of the reference object is made from polyamide 6 and/or polyamide 6,6.

4. Process according to claim 1, wherein separate detecting means are used for detecting when a reference object is in front of the optical spectrometer.

5. Process according to claim 4, wherein a predetermined surface of the articles and/or said at least one external reference object is irradiated and wherein the process further comprises d) determining when the predetermined surface of the articles and/or said at least one external reference object is in front of the spectrometer, and further wherein the irradiation, measuring the response, and/or analyzing the response is started for each article and/or said at least one external reference object individually, while the predetermined surface of said individual article and/or said at least one external reference object is in front of the spectrometer.

6. Process according to claim 1, wherein the optical spectrometer is an infrared spectrometer.

7. Process according to claim 1, wherein at least part of the articles are at least partly made from a polyamide.

8. Process according to claim 7, wherein the surface material of said at least one external reference object is made from one of the polymers to be identified.

9. Process according to claim 1, wherein at least part of the articles are at least partly made from a polyamide-6 and/or that at least part of the articles are at least partly made from polyamide-6,6.

10. Process according to claim 9, wherein the surface material of said at least one external reference object is made from one of the polymers to be identified.

11. Process according to claim 1, wherein the articles are textile articles.

12. Process according to claim 11, wherein the textile articles are carpets or carpet materials.

13. Process according to claim 12, wherein the surface material of said at least one external reference object is made from one of the polymers to be identified.

14. Process according to claim 11, wherein the surface material of said at least one external reference object is made from one of the polymers to be identified.

15. Apparatus useful for identifying articles which are at least partly made from at least one polymer, said apparatus comprising:
    a) an optical spectrometer
    b) a transport system, said transport system comprising a transport rail and transport units, the transport units comprising a body, coupling means for fixing the articles to the transport units, the transport units being movably connected to the transport rail
    c) a guide system which is capable of cooperating with the body and/or coupling means, said guide system at least being present in the area of the optical spectrometer, wherein the guide system comprises a pair of guiding elements which are essentially parallel to the transport rail and which are capable of receiving the body and/or coupling means.

16. Apparatus according to claim 15, wherein the guide system comprises a guiding element which is essentially parallel to the transport rail, said guiding element being capable of cooperating with the body and/or coupling means.

17. Apparatus according to claim 16, wherein said one or more guiding members are rotatable elements.

18. Apparatus according to claim 15, wherein the body and/or coupling means comprise one or more guiding members which can cooperate with the guiding element.

19. Apparatus according to claim 15, wherein the guide system is a transversal guide system.

20. Apparatus according to claim 15, wherein the guide system is a longitudinal guide system.

21. Apparatus according to claim 15, wherein the optical spectrometer is an infrared spectrometer.

22. Apparatus according to claim 15, wherein the coupling means have openings through which an article which is coupled with said coupling means can be irradiated with an irradiation beam.

* * * * *